(12) United States Patent
Deng et al.

(10) Patent No.: US 10,739,434 B2
(45) Date of Patent: Aug. 11, 2020

(54) ACOUSTIC TRANSMISSION DEVICE AND PROCESS FOR TRACKING SELECTED HOSTS

(71) Applicant: Battelle Memorial Institute, Richland, WA (US)

(72) Inventors: Zhiqun Deng, Richland, WA (US); Huidong Li, Richland, WA (US); Jun Lu, Richland, WA (US); Mitchell J. Myjak, Richland, WA (US); Jayson J. Martinez, Richland, WA (US); Jie Xiao, Richland, WA (US); Richard S. Brown, Richland, WA (US); Samuel S. Cartmell, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/143,273

(22) Filed: Sep. 26, 2018

(65) Prior Publication Data

US 2019/0018100 A1    Jan. 17, 2019

Related U.S. Application Data

(63) Continuation of application No. 14/631,587, filed on Feb. 25, 2015, now Pat. No. 10,101,429.

(51) Int. Cl.
*G01S 1/72* (2006.01)
*G01S 5/18* (2006.01)
(Continued)

(52) U.S. Cl.
CPC .............. *G01S 1/72* (2013.01); *A01K 11/006* (2013.01); *A01K 61/90* (2017.01); *A61B 5/0015* (2013.01);
(Continued)

(58) Field of Classification Search
CPC combination set(s) only.
See application file for complete search history.

(56) References Cited

U.S. PATENT DOCUMENTS 2,775,939 A    1/1957    Fogal
3,100,866 A    8/1963    Marks
(Continued)

FOREIGN PATENT DOCUMENTS

CA    2091043    9/1994
CN    1424592    6/2003
(Continued)

OTHER PUBLICATIONS

Deng et al., U.S. Appl. No. 16/193,968, filed Nov. 16, 2018, titled "Methods for Attaching Transmitters to Animals", 51 pages.
(Continued)

*Primary Examiner* — Hovhannes Baghdasaryan
*Assistant Examiner* — Amie M Ndure
(74) *Attorney, Agent, or Firm* — Wells St. John P.S.

(57) ABSTRACT

A new acoustic tag and process are disclosed for identifying and tracking underwater hosts in up to three dimensions. The acoustic tag has an operation lifetime up to a year or longer at a pulse rate interval of about 15 seconds. The acoustic tag has a signal detection range up to at least about 500 meters that enhances detection probability.

22 Claims, 6 Drawing Sheets

(51) Int. Cl.
*A61B 5/07* (2006.01)
*G06K 17/00* (2006.01)
*H04B 1/034* (2006.01)
*A01K 11/00* (2006.01)
*A61B 5/00* (2006.01)
*A61B 5/11* (2006.01)
*A01K 61/90* (2017.01)
*G06K 19/07* (2006.01)

(52) U.S. Cl.
CPC .............. *A61B 5/07* (2013.01); *A61B 5/1112* (2013.01); *G01S 5/18* (2013.01); *G06K 17/00* (2013.01); *H04B 1/034* (2013.01); *A61B 2503/40* (2013.01); *A61B 2562/08* (2013.01); *G06K 19/0728* (2013.01)

(56) References Cited

U.S. PATENT DOCUMENTS

| | | | |
|---|---|---|---|
| 3,100,886 A * | 8/1963 | Marks | B06B 1/0269 367/137 |
| 3,262,093 A * | 7/1966 | Junger | B06B 1/0655 367/159 |
| 3,292,303 A | 12/1966 | Fors | |
| 3,311,830 A * | 3/1967 | Skirvin | H03C 5/00 455/102 |
| 3,576,732 A | 4/1971 | Weidinger et al. | |
| 3,713,086 A | 1/1973 | Trott | |
| 4,042,845 A | 8/1977 | Hackett | |
| 4,241,535 A | 12/1980 | Tsukuda | |
| 4,259,415 A | 3/1981 | Tamura et al. | |
| 4,336,709 A | 6/1982 | Meek | |
| 4,353,004 A * | 10/1982 | Kleinschmidt | G01S 7/524 310/317 |
| 4,392,236 A | 7/1983 | Sandstrom et al. | |
| 4,679,559 A | 7/1987 | Jefferts | |
| 4,762,427 A | 8/1988 | Hori et al. | |
| 4,790,090 A | 12/1988 | Sharber | |
| 4,970,988 A | 11/1990 | Heisey | |
| 4,986,276 A * | 1/1991 | Wright | A61B 8/06 600/437 |
| 5,177,891 A | 1/1993 | Holt | |
| 5,211,129 A | 5/1993 | Taylor et al. | |
| 5,324,940 A | 6/1994 | Ekstrom | |
| 5,344,357 A | 9/1994 | Lyczek | |
| 5,517,465 A | 5/1996 | Nestler et al. | |
| 5,675,555 A | 10/1997 | Evans et al. | |
| 5,697,384 A | 12/1997 | Miyawaki et al. | |
| 5,857,881 A | 1/1999 | Zippel, Sr. | |
| 5,974,304 A * | 10/1999 | Chen | H04B 1/086 455/351 |
| 5,995,451 A | 11/1999 | Evans et al. | |
| 6,021,731 A | 2/2000 | French et al. | |
| 6,201,766 B1 | 3/2001 | Carlson et al. | |
| 6,662,742 B2 | 12/2003 | Shelton et al. | |
| 6,712,772 B2 | 3/2004 | Cohen et al. | |
| 6,928,765 B2 | 8/2005 | Brickett | |
| 7,016,260 B2 | 3/2006 | Baray | |
| 7,289,931 B2 | 10/2007 | Ebert | |
| 7,457,720 B2 | 11/2008 | Ebert | |
| 8,032,429 B2 | 10/2011 | Shafer | |
| 8,033,890 B2 | 10/2011 | Warner et al. | |
| 8,360,327 B2 | 1/2013 | Clarke | |
| 8,448,592 B2 | 5/2013 | Crowell et al. | |
| 8,564,985 B2 * | 10/2013 | van Straaten | H02M 1/44 363/60 |
| 9,266,591 B2 | 2/2016 | Lu | |
| 10,033,469 B2 | 7/2018 | Deng et al. | |
| 10,033,470 B2 | 7/2018 | Deng et al. | |
| 10,067,112 B2 | 9/2018 | Deng et al. | |
| 10,101,429 B2 * | 10/2018 | Deng | A61B 5/0015 |
| 2003/0117893 A1 | 6/2003 | Baray | |
| 2003/0128847 A1 * | 7/2003 | Smith | A61B 7/04 381/67 |
| 2004/0133081 A1 * | 7/2004 | Teller et al. | |
| 2006/0218374 A1 | 9/2006 | Ebert | |
| 2007/0083119 A1 * | 4/2007 | Adachi | A61B 8/12 600/437 |
| 2007/0088194 A1 | 4/2007 | Tahar et al. | |
| 2007/0103314 A1 | 5/2007 | Geissler | |
| 2007/0288160 A1 | 12/2007 | Ebert | |
| 2008/0269614 A1 * | 10/2008 | Adachi | A61B 8/00 600/459 |
| 2009/0073802 A1 | 3/2009 | Nizzola et al. | |
| 2009/0079368 A1 * | 3/2009 | Poppen | H02M 1/4208 318/254.1 |
| 2009/0188320 A1 * | 7/2009 | Greenough | G01N 29/11 73/602 |
| 2011/0105829 A1 | 5/2011 | Ball | |
| 2011/0163857 A1 | 7/2011 | August et al. | |
| 2011/0181399 A1 | 7/2011 | Pollack et al. | |
| 2011/0254529 A1 * | 10/2011 | van Straaten | H02M 1/44 323/311 |
| 2012/0134239 A1 * | 5/2012 | Struthers | H04B 1/034 367/137 |
| 2012/0277550 A1 | 11/2012 | Rosenkranz et al. | |
| 2013/0012865 A1 | 1/2013 | Sallberg et al. | |
| 2013/0181839 A1 | 7/2013 | Cao | |
| 2013/0324059 A1 | 12/2013 | Lee et al. | |
| 2014/0211594 A1 | 7/2014 | Allen et al. | |
| 2015/0063072 A1 | 3/2015 | Deng et al. | |
| 2015/0241566 A1 | 8/2015 | Chakraborty et al. | |
| 2015/0289479 A1 | 10/2015 | Allen et al. | |
| 2016/0211924 A1 | 7/2016 | Deng et al. | |
| 2016/0245894 A1 | 8/2016 | Deng et al. | |
| 2017/0089878 A1 | 3/2017 | Deng et al. | |
| 2017/0164581 A1 | 6/2017 | Deng et al. | |
| 2017/0170850 A1 | 6/2017 | Deng et al. | |
| 2018/0055007 A1 | 3/2018 | Deng et al. | |

FOREIGN PATENT DOCUMENTS

| | | |
|---|---|---|
| CN | 102568463 | 7/2012 |
| CN | 102598716 | 7/2012 |
| CN | 202414143 | 9/2012 |
| CN | 102754249 | 10/2012 |
| CN | 2014800479315 | 7/2017 |
| EP | 2037396 A1 | 3/2009 |
| EP | 1705500 B1 | 6/2010 |
| GB | 1195633 A | 6/1970 |
| GB | 2188028 A | 9/1987 |
| JP | 61-291294 | 12/1986 |
| WO | WO 95/03691 | 2/1995 |
| WO | WO 2011/068825 | 6/2011 |
| WO | WO 2011/079338 | 7/2011 |
| WO | PCT/US2014/05357 B | 12/2014 |
| WO | PCT/US2014/053578 | 3/2015 |
| WO | WO 2015/031853 | 3/2015 |
| WO | PCT/US2015/062200 | 2/2016 |
| WO | PCT/US2014/053578 | 3/2016 |
| WO | PCT/US2016/054981 | 11/2016 |
| WO | PCT/US2016/055045 | 2/2017 |
| WO | PCT/US2015/062200 | 8/2017 |
| WO | PCT/US2017/038082 | 9/2017 |
| WO | PCT/US2017/038082 | 11/2017 |
| WO | PCT/US2016/054981 | 6/2018 |
| WO | PCT/US2016/055045 | 6/2018 |

OTHER PUBLICATIONS

Aktakka et al., "Energy Scavenging from Insect Flight", Journal of Micromechanics and Microengineering vol. 21, 095016, 2011, United Kingdom, 10 pages.

Brown et al., "An Evaluation of the Maximum Tag Burden for Implantation of Acoustic Transmitters in Juvenile Chinook Salmon", North American Journal of Fisheries Management vol. 30, 2010, United States, pp. 499-505.

Cha et al., "Energy Harvesting from a Piezoelectric Biomimetic Fish Tail", Renewable Energy vol. 86, 2016, Netherlands, pp. 449-458.

(56) References Cited

OTHER PUBLICATIONS

Cha et al., "Energy Harvesting from the Tail Beating of a Carangiform Swimmer using Ionic Polymer-Metal Composites", Bioinspiration and Biomimetics vol. 8, 2013, United Kingdom, 15 pages.
Cook et al., "A Comparison of Implantation Methods for Large PIT Tags or Injectable Acoustic Transmitters in Juvenile Chinook Salmon", Fisheries Research vol. 154, 2014, Netherlands, pp. 213-223.
Dagdeviren et al., "Conformal Piezoelectric Energy Harvesting and Storage from Motions of the Heart, Lung, and Diaphragm", Proceedings of the National Academy of Sciences of the United States of America vol. 111, 2014, United States, pp. 1927-1932.
Deng et al., "A Cabled Acoustic Telemetry System for Detecting and Tracking Juvenile Salmon: Part 2. Three-Dimensional Tracking and Passage Outcomes", Sensors vol. 11, 2011, Switzerland, pp. 5661-5676,
Deng et al., "An Injectable Acoustic Transmitter for Juvenile Salmon", Scientific Reports, Jan. 29, 2015, United Kingdom, 6 pages.
Deng et al., "Design and Instrumentation of a Measurement and Calibration System for an Acoustic Telemetry System", Sensors vol. 10, 2010, Switzerland, pp. 3090-3099.
Deng et al., U.S. Appl. No. 62/267,738, filed Dec. 15 2015, titled "Transmitters for Animals and Methods for Transmitting from Animals", 42 pages.
Deng et al., U.S. Appl. No. 62/267,797, filed Dec. 15, 2015, titled "Signal Transmitter and Methods for Transmitting Signals from Animals", 34 pages.
Eppard, "Juvenile Salmon Acoustic Telemetry System JSATS", Dec. 14, 2011, URL: http://www.nwcouncil.org/media/23478/jsats.pdf, pp. 1-13.
Erturk et al., "Underwater Thrust and Power Generation Using Flexible Piezoelectric Composites: An Experimental Investigation Toward Self-Powered Swimmer-Sensor Platforms", Smart Materials and Structures vol. 20, 125013, 2011, United Kingdom, 11 pages.
Hwang et al., "Powered Cardiac Pacemaker Enabled by Flexible Single Crystalline PMN-PT Piezoelectric Energy Harvester", Advanced Materials vol. 26, 2014, Germany, pp. 4880-4887.
Hwang et al., "Self-Powered Deep Brain Stimulation via a Flexible PIMNT Energy Harvester", Energy and Environmental Science vol. 8, 2015, United Kingdom, pp. 2677-2684.
Lam et al., "Physical Characteristics and Rate Performance of $(CFx)_n$ $(0.33>x>9,66)$ in Lithium Batteries", Journal of Power Sources vol. 153, 2006, Netherlands, pp. 354-359.
Li et al., "Design Parameters of a Miniaturized Piezoelectric Underwater Acoustic Transmitter", Sensors vol. 12, 2012, Switzerland, pp. 9098-9109.
Li et al., "Energy Harvesting from Low Frequency Applications using Piezoelectric Materials", Applied Physics Reviews 1, 041301, 2014, United States, 20 pages.
Li et al., "Piezoelectric Materials Used in Underwater Acoustic Transducers" Sensor Letters vol. 10 (3/4), 2012, United States, pp. 679-697.
Li et al., "Piezoelectric Transducer Design for a Miniaturized Injectable Acoustic Transmitter", Smart Materials and Structures vol. 24, 115010, 2015, United Kingdom, 9 pages.
McMichael et al., "The Juvenile Salmon Acoustic Telemetry System: A New Tool", Fisheries vol. 35, No. 1, Jan. 1, 2010, United States, pp. 9-22.
Meduri et al., "Hybrid $CVx-Ag_2V_4O_{11}$ as a High-Energy, Power Density Cathode for Application in an Underwater Acoustic Microtransmitter", Electrochemistry Communications vol. 13, 2011, United States, pp. 1344-1348.
Ritchie et al., "Further Developments of Lithium/Polycarbon Monofluoride Envelope Cells", Journal of Power Sources vol. 96, 2001, Netherlands, pp. 180-183.
Rub et al., "Comparative Performance of Acoustic-Tagged and Passive Integrated Transponder-Tagged Juvenile Salmonids in the Columbia and Snake Rivers", U.S. Army Corps of Engineers, Portland District, Portland Oregon, 2007, United States, 163 pages.
S.M. Corporation, "Macro Fiber Composite—MFC" Smart Material Brochure, United States, 8 pages.
Shafer, "Energy Harvesting and Wildlife Monitoring", available online at http://www.ofwim.org/wp-content/uploads/2014/11/Shafer_keynote.pdf, 2014, 36 pages.
Weiland et al., "A Cabled Acoustic Telemetry System for Detecting and Tracking Juvenile Salmon: Part 1. Engineering Design and Instrumentation", Sensors vol. 11, No. 12, Dec. 26, 2011, Switzerland, pp. 5645-5660.
Yazami et al., "Fluorinated Carbon Nanofibres for High Energy and High Power Densities Primary Lithium Batteries", Electrochemistry Communications vol. 9, 2007, Netherlands, pp. 1850-1855.
Zhang et al., "Enhancement of Discharge Performance of Li/CFx Cell by Thermal Treatment of CFx Cathode Material", Journal of Power Sources vol. 188, 2009, Netherlands, pp. 601-605.
Adams et al., "Effects of Surgically and Gastrically Implanted Radio Transmitters on Swimming Performance and Predator Avoidance of Juvenile Chinook Salmon (*Oncorhynchus tshawytscha*)", Canadian Journal of Fisheries and Aquatic Sciences 55, 1998, Canada, pp. 781-787.
Angela et al., "Effects of Acoustic Transmitters on Swimming Performance and Predator Avoidance of Juvenile Chinook Salmon", North American Journal of Fisheries Management 24, 2004, United States, pp. 162-170.
Atlantic States Marine Fisheries Commission, "American Eel Benchmark Stock Assessment Report No. 12-01", May 2012, United States, 340 pages.
Bams, "Differences in Performance of Naturally and Artificially Propagated Sockeye Salmon Migrant Fry, as Measured with Swimming and Predation Tests", Journal of the Fisheries Board of Canada 24(5), 1967, Canada, pp. 1117-1153.
Barbin et al., "Behaviour and Swimming Performance of Elvers of the American Eel, Anguilla Rostrata, in an Experimental Flume", Journal of Fish Biology 45, 1994, United Kingdom, pp. 111-121.
Biopack Systems, Inc. Hardware Guide, 2013, 152 pages.
Boubee et al., "Downstream Passage of Silver Eels at a Small Hydoelectric Facility", Fisheries Management and Ecology vol. 13, 2006, United Kingdom, pp. 165-176.
Brett, "The Respiratory Metabolism and Swimming Performance of Young Sockeye Salmon", Journal of the Fisheries Board of Canada 21(5), 1964, Canada, pp. 1183-1226.
Brown et al., "Evidence to Challenge the "2% Rule" for Biotelemetry", North American Journal of Fisheries Management 19, 1999, United States, pp. 867-871.
Brown et al., "Survival of Seaward-Migrating PIT and Acoustic-Tagged Juvenile Chinook Salmon in the Snake and Columbia Rivers: An Evaluation of Length-Specific Tagging Effects", Animal Biotelemetry 1:8, 2013, United States, 13 pages.
Brown, "Design Considerations for Piezoelectric Polymer Ultrasound Transducers", IEEE Transactions on Ultrasonics, Ferroelectrics, and Frequency Control vol. 47, No. 6, Nov. 2000, United States, pp. 1377-1396.

\* cited by examiner

ACOUSTIC TRANSMISSION DEVICE AND PROCESS FOR TRACKING SELECTED HOSTS

RELATED PATENT DATA

This application is a continuation of and claims priority to U.S. patent application Ser. No. 14/631,587, which was filed Feb. 25, 2015, the teachings of which are incorporated herein by reference.

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

The present invention relates generally to acoustic tracking devices and systems. More particularly, the present invention relates to attachable acoustic transmission devices for detection and remote tracking of smaller hosts both inanimate and animate in up to three dimensions in real-time or as a function of time.

BACKGROUND OF THE INVENTION

Acoustic telemetry involves acoustic devices (or tags) commonly used to monitor behavior of fish. Acoustic tags transmit a sound signal that transmits identification, location, and other information about a tagged fish to a receiver at a selected pulse rate interval (PRI), or "ping" rate. The receiver detects signals emitted by the acoustic tag and converts the sound signals into digital data. Post-processing software then processes the digital data and provides location information about the tag and thus the behavior of the fish when the receiver detects the sound signal. By identifying the signature of the acoustic signal a specific animal may be identified, which allows tracking the behavior of the host. Acoustic data may be used, e.g., to estimate survival of fish through dams and other routes of passage. However, conventional transmitters are too large for small hosts (30-100 g mass and 180-270 mm length), have short lifetimes, and/or have an inadequate transmission range that to date have precluded intensive research of small hosts such as juvenile sturgeon using acoustic telemetry techniques. Recently, an injectable acoustic tag was developed for the U.S. Army Corps of Engineers for tracking juvenile salmon detailed in U.S. patent application Ser. No. 14/014,035 filed 29 Aug. 2013, and other acoustic tags for tracking other small hosts detailed in Patent Application No.: PCT/US14/53578 filed 29 Aug. 2014, which references are incorporated herein in their entirety. The injectable acoustic tag works well for tracking yearling Chinook salmon in river systems. However, it is not optimal for long-term monitoring of hosts requiring a stronger acoustic signal and longer service life including, e.g., juvenile (<1 year old) sturgeon. Accordingly, new tag designs are needed that reduce the overall size, mass, and/or volume, that enhance the power source voltage, tag lifetimes, and transmission range, and reduce adverse effects and costs associated with attachment (which includes implantation) thus broadening the range of potential applications including, e.g., investigating behavior and habitat of juvenile sturgeon and other small species. The present invention addresses these needs.

SUMMARY OF THE INVENTION

The present invention includes a new acoustic transmission device (acoustic tag) and a process for remotely tracking various hosts in up to three dimensions in real-time or as a function of time. The acoustic tag may include a power source that delivers a power source voltage to power a tag circuit. The tag circuit may deliver a selected voltage to a piezoelectric transducer (PZT) that transmits an acoustic transmission signal at a signal intensity selected between about 159 dB and about 163 dB. The tag may be configured to provide a selectable tag lifetime at the selected signal intensity of at least about 98 days at a pulse rate interval of about 5 seconds.

The present invention also includes a method for tracking selected hosts. The method may include delivering a selected voltage from a tag circuit powered by a power source to PZT in the acoustic transmission (tag) device. The tag device may be attached to the selected host. The tag circuit may generate an acoustic transmission signal in the PZT at a selected signal intensity over a selectable tag lifetime. Signal intensity may be selected between about 159 dB and about 163 dB.

In some embodiments, the tag lifetime may be at least about 365 days at a transmission (ping) rate of about 15 seconds at a signal intensity of 161 dB.

In some embodiments, the tag lifetime may be at least about 249 days at a transmission (ping) rate of 10 seconds at a signal intensity of 161 dB.

In some embodiments, the tag lifetime may be about 156 days at a pulse rate interval of about 5 seconds and an acoustic signal intensity of 159 dB.

In some embodiments, the acoustic tag may include a power source that delivers a selectable power source voltage that powers components of the acoustic tag located on, or coupled to, a tag circuit. In various embodiments, the power source voltage may be selected between about 1.8 V and about 3.0 V.

In some embodiments, the tag circuit may include a dual boost converter sub-circuit that couples to two analog switches. In some embodiments, one of the analog switches may be coupled to the PZT through an inductor. The other analog switch may be coupled directly to the PZT. This configuration allows a higher peak-to-peak voltage from the tag circuit to be delivered across the PZT than would normally be delivered to the PZT. In some embodiments, the two analog switches may be directly coupled to the PZT, which permits the voltage from the tag circuit to be directly applied to the PZT.

In some embodiments, the dual boost converter sub-circuit may transform the voltage delivered from the power source into two output voltages. One output voltage may be a higher voltage (e.g., about +7 volts) than the power source voltage. The other output voltage may be a lower voltage (e.g., about −3 volts) than the power source voltage. The dual boost converter sub-circuit may share a single inductor to reduce the size of the tag.

The dual boost converter sub-circuit may alternately switch between the two voltage potentials in succession and deliver the two voltages through the respective analog switches to generate a selectable output voltage from the tag circuit to the PZT that drives transmission of the acoustic signal from the acoustic tag. In the exemplary embodiment, when the two voltage potentials delivered by the dual boost converter sub-circuit alternate between about +7 volts and about −3 volts, the voltage delivered from the tag circuit to the PZT may be about 20 volts (peak-to-peak).

The method may include delivering the selected (drive) voltage from the tag circuit from a boost conversion sub-circuit within the tag circuit across an inductor to the PZT.

In some embodiments, the energy expenditure for transmission of the acoustic signal from the piezoelectric transducer may be less than or equal to about 385 µJ per transmission at a signal intensity of 163 dB.

In some embodiments, the energy expenditure for transmission of the acoustic signal from the piezoelectric transducer may be less than or equal to about 283 µJ per transmission at a signal intensity of 161 dB.

In some embodiments, the acoustic signal may include a transmission range of at least about 500 meters at full intensity.

In some embodiments, the new acoustic device (tag) may include a length at or below about 24.2 mm, a diameter at or below about 5.0 mm, and a dry weight of less than about 0.72 grams.

The method may include attaching the acoustic tag to the selected host at a selected location.

The acoustic signal may be encoded with one or more tag codes of a selected code length. The acoustic signal may contain location data, identification data about the host, and/or sensor data that may all be transmitted from the acoustic tag to a receiver located external to the host.

The method may also include decoding the acoustic signal received from the acoustic tag to identify and track the host in up to three dimensions in real-time or as a function of time.

The acoustic transmission device may be configured for tracking a sturgeon host or another underwater host.

The foregoing summary is neither intended to define the invention of the application, which is measured by the claims, nor is it intended to be limiting as to the scope of the invention in any way.

DETAILED DESCRIPTION

A new acoustic transmission (tag) device and process are disclosed for identification and remote tracking of various small hosts including, e.g., juvenile sturgeon, and other deep-water and underwater hosts in up to three dimensions (3D) (i.e., X-Y-Z coordinates). In the following description, embodiments of the present invention are described by way of illustration of the best mode contemplated for carrying out the invention. Various components including, e.g., a transducer, tag and drive circuitry, and a power source are described that address specific performance requirements (e.g., size, mass, signal intensity, range, and tag lifetime). It will be apparent that the invention is amenable to various permutations, modifications, and alternative constructions. It should be understood that there is no intention to limit the present invention to specific forms disclosed herein, but, on the contrary, the present invention is to intended cover all modifications, alternative constructions, and equivalents falling within the scope of the present invention as defined in the claims. Therefore the description should be seen as illustrative and not limiting.

Acoustic tags of the present invention may include various form factors and shapes that allow the tags to be attached to selected hosts for selected applications. However, shapes are not intended to be limited. The term "form factor" used herein refers to the physical arrangement, configuration, and dimensions of electrical components in the acoustic tags and the capsule that contains the device components. The term "host" refers to inanimate or animate objects to which the acoustic tag may be attached for tracking and/or identification. Inanimate hosts include, but are not limited to, e.g., propelled objects (e.g., robots), stationary objects, moveable objects, and transportable objects. Animate hosts may include, but are not limited to, e.g., aquatic species including, e.g., marine and freshwater animals, deep water hosts (e.g., juvenile sturgeon, lamprey, and eels), divers, underwater mammals, and other living hosts. The present invention will now be described with reference to tracking of an exemplary deep-water host, i.e., juvenile sturgeon. However, it should be understood that the invention is not intended to be limited thereto. As discussed above, acoustic tags of the present invention are well suited for a wide variety of applications and tracking of different hosts. No limitations are intended.

Figure 1:
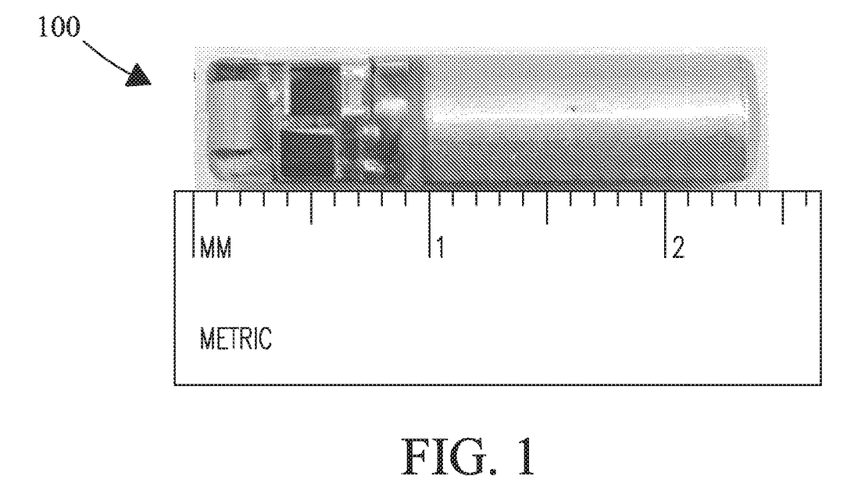
FIG. 1 shows an acoustic transmission device of the present invention and associated length dimensions.

FIG. 1 is a perspective view of a new acoustic transmission device (acoustic tag) 100 of the present invention. In the exemplary embodiment, acoustic tag 100 may include an elongated or cylindrical shape that permits the tag to be easily implanted in, or attached to, the selected host. Approaches for attachment are not limited. TABLE 1 lists exemplary parameters of the new acoustic tag.

TABLE 1

| | |
|---|---|
| Dimensions (Length × Diameter): | 24.2 mm × Ø5.0 mm* |
| Dry Weight: | 720 mg |
| Volume: | 429 mm³ |
| Source Level: | 159-163 dB (re: 1 µPa @ 1 meter) |
| Tag lifetime: | 98-156 days at 5-second pulse rate interval (163 dB and 159 dB, respectively) |
| Tag lifetime: | 285-365 days at 15-second pulse rate interval (163 dB and 161 dB, respectively) |
| Transmission Range: | Up to 500 meters (163 dB) |

*Ø is an engineering unit for diameter, given here in millimeters.

In the exemplary embodiment, tag 100 may include a length of 24.2 mm and a maximum diameter of 5.0 mm. The front end of the tag may include a narrower dimension than the back end of the tag and may include a relatively flat profile to minimize weight of the tag. The acoustic tag includes a compact volume, and a mass of about 720 mg in air. Tag 100 further includes a unique tag circuit that drives transmission of the acoustic signal from the PZT, a power source with a greater power output, an enhanced and adjustable acoustic signal intensity (or source level), a selectable and longer tag lifetime, and a longer transmission range for tracking selected hosts. The acoustic transmission signal may be adjusted to provide various detection ranges and tag lifetimes.

Figure 2:
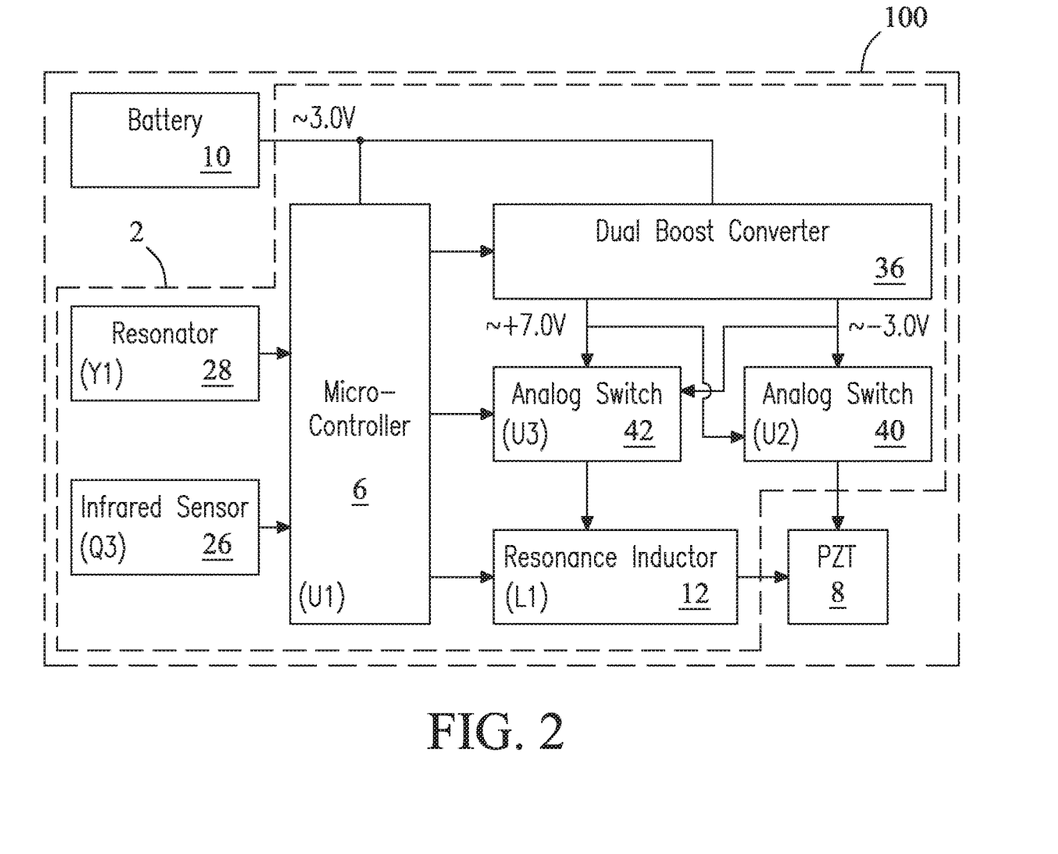
FIG. 2 is a block diagram showing components of the acoustic transmission device.

FIG. 2 is a block diagram showing exemplary components of acoustic tag 100 of the present invention and associated electrical inputs and outputs. Tag 100 may include a power source (e.g., battery) 10 that powers components of the acoustic tag. Power source 10 may be a custom lithium carbon fluoride battery of a similar design to that described in U.S. application Ser. No. 14/014,035. Each laminate may include an anode and a cathode positioned between polymer separators that electrically isolate the cathode from the anode in the laminate. The separator may include micro-porous polypropylene. The cathode may include, or be constructed of, e.g., carbon fluoride and a conducting carbon within a binder affixed at a selected thickness to a current collector. The binder may include, e.g., polytetrafluoroethylene (PTFE). The anode may be constructed of lithium metal. The power source may be filled with an electrolyte such as, e.g., lithium hexafluorophosphate (LiPF$_6$) disbursed in a selected volume ratio of ethylene carbonate (EC) and dimethyl carbonate (DMC). In the exemplary embodiment, power source may be of a larger size that provides a greater power output of up to about 80 mAh and a longer tag lifetime. In the instant design, power source 10 may include a plurality of laminates configured to supply a selectable output voltage between about 1.8 volts (1.8 V) to about 3.0 volts (3.0 V).

Tag 100 may also include a programmable microcontroller 6 (U1) (e.g., a model PIC16F1823T/CL 8-bit, 8K flash, programmable microcontroller in a chip-scale package, Microchip Technology, Chandler, Ariz., USA) that provides operational control of components of acoustic tag 100. Tag components are configured to generate and deliver an acoustic signal at a desired modulation or resonance frequency (e.g., 416.7 kHz) that is transmitted from the acoustic tag.

Resonator 28 (Y1) (e.g., a model CSTCE10M0G52-R0, 10 MHz ceramic resonator, Murata Manufacturing Co., Ltd., Nagaokakyo, Kyoto Prefecture, Japan) may be coupled on the input side of microcontroller 6 (U1) to generate a clock signal of a selected precision (e.g., ±0.5% tolerance or better) that controls operation of controller (U1) 6 and other components of acoustic tag 100.

A phototransistor (Q3) 26 (e.g., a model PT19-21B, flat black mini SMD phototransistor, Everlight Electronics Co., Ltd., New Taipei City, Taiwan) sensitive to optical or infrared radiation may be coupled on the input side of microcontroller 6 to receive configuration commands from an external computer.

Tag 100 may further include a dual boost converter sub-circuit 36 that couples to two analog switches 40 (U2) and 42 (U3). Analog switch 42 (U3) may be coupled to a high-efficiency resonance inductor 12 (L1) (e.g., a 10 uH, 80 MAmp, 20% tolerance inductor, Coilcraft, Cary, Ill., USA). Analog switch 40 (U2) and resonance inductor 12 (L1) may be coupled to piezoelectric transducer 8. The dual boost converter sub-circuit, two analog switches, and resonance inductor together generate a drive voltage that drives transmission of the acoustic signal from piezoelectric transducer 8 at a selected modulation or resonance frequency, e.g., 416.7 kHz.

Dual boost converter sub-circuit 36 also controls the intensity of the acoustic signal delivered from piezoelectric transducer 8. The signal intensity is selectable between about 159 dB and about 163 dB. Selection of the power source voltage and the acoustic signal intensity provides a selectable tag lifetime.

Figure 3A:
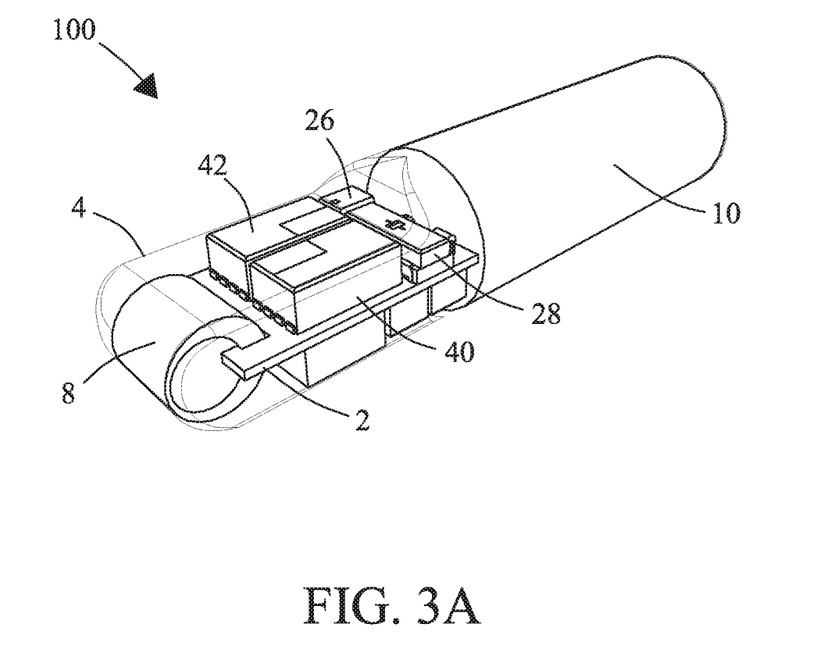
FIGS. 3A-3B are different top views of the present invention.
Figure 4A:
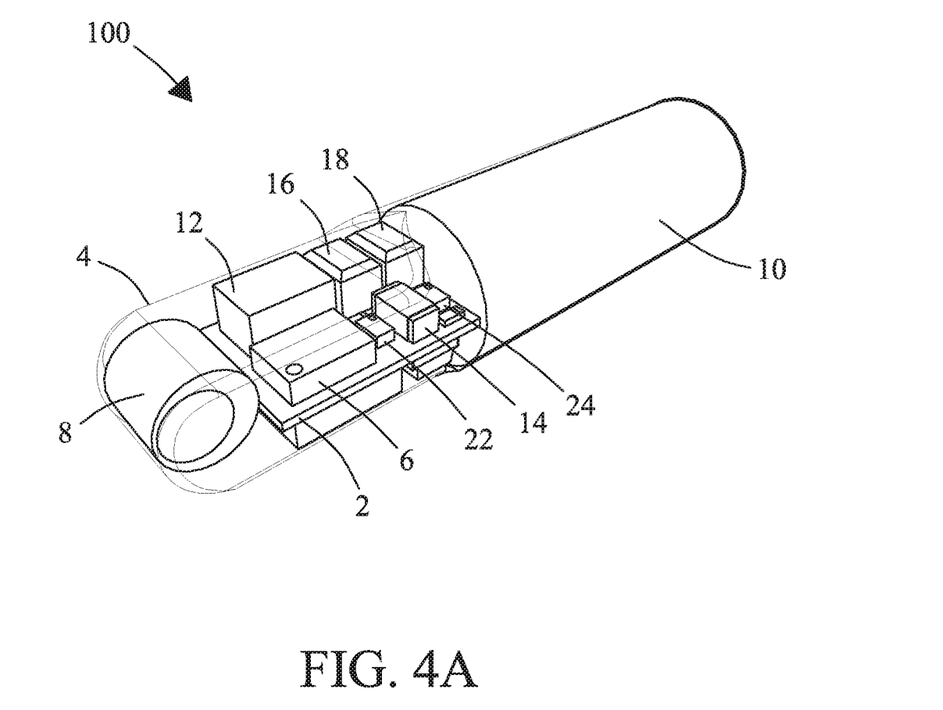
FIGS. 4A-4B are different bottom views of the present invention.

Components of tag 100 may be selected to reduce physical dimensions and weight of the tag, and may be coupled to both sides of a circuit board 2 as shown in FIG. 3A and FIG. 4A described hereafter. Circuit board 2 may be constructed of rigid board materials (~0.02 cm thickness) such as FR4 boards, or flexible board materials (~0.01 cm thickness) such as flex boards.

Figure 3B:
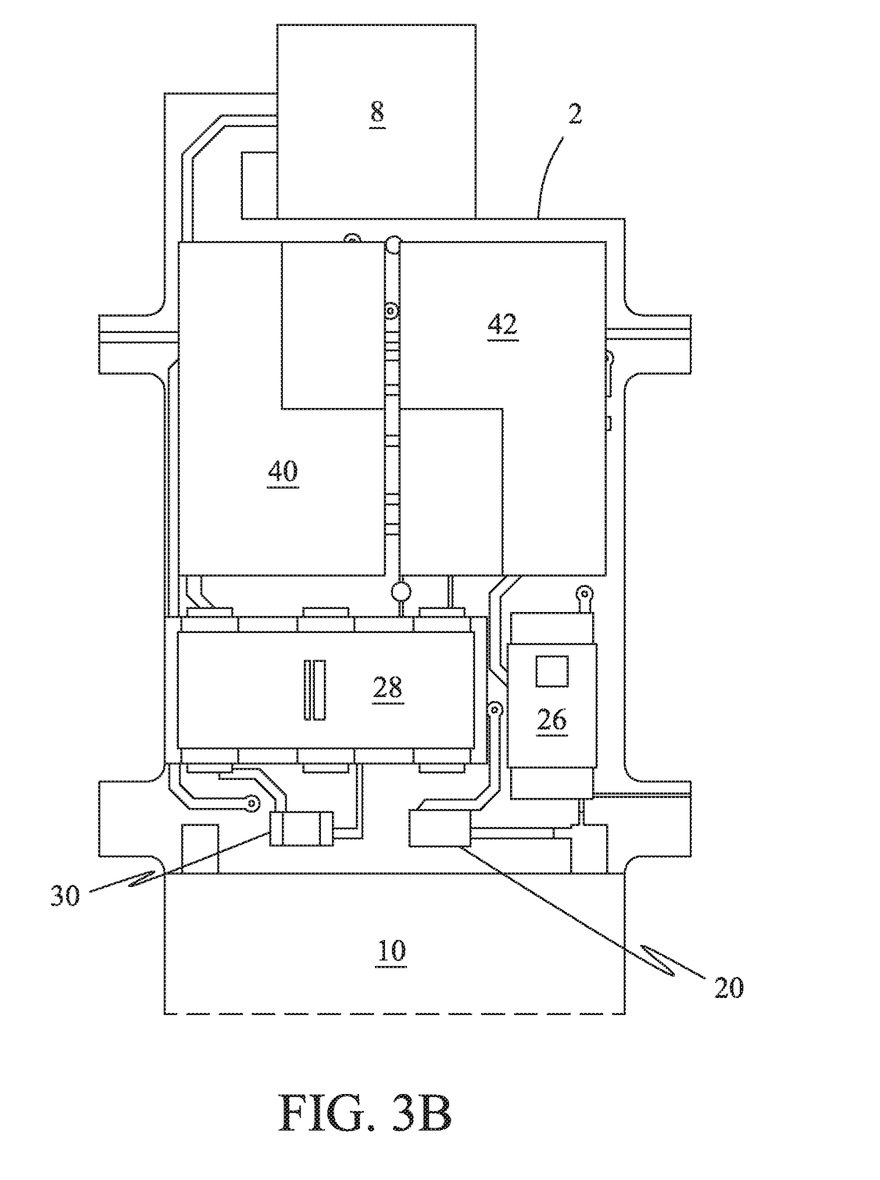

FIGS. 3A-3B present different top-side views of circuit board 2 showing position of selected components of acoustic tag 100. In these figures, piezoelectric transducer 8 is shown electrically coupled to circuit board 2, e.g., at a forward end of acoustic tag 100 such that the acoustic signal may be transmitted free of interference from or obstruction by other tag components. Power source 10 may be coupled to circuit board 2 at an end opposite piezoelectric transducer 8 to power operation of piezoelectric transducer 8 and other tag components. However, location is not intended to be limited.

Resonator 28 (Y1) (e.g., a 10 MHz ceramic resonator described previously in reference to FIG. 2) may be coupled to microcontroller 6 to control timing of operation of tag components. Phototransistor 26 (Q3) may be positioned to receive configuration commands from a source computer. Analog switches 40 (U2) and 42 (U3) may be positioned to deliver a drive voltage to PZT 8 of about 20 volts (peak-to-peak) directly to piezoelectric transducer 8, or to deliver the same drive voltage across a resonance inductor 12 (L1) to piezoelectric transducer 8 as described previously herein.

Tag 100 components may be encapsulated within a coating composed of a thermosetting polymer such as an epoxy (e.g., EPO-TEK® 301 epoxy, Epoxy Technology Inc., Bellerica, Mass., USA) or a resin (e.g., Scotchcast® Electrical Resin 5, 3M Company, St. Paul, Minn., USA) that forms a capsule 4.

In FIG. 3B, a resistor 30 (R1) (e.g., a 1.0 Mohm, 1/20 W, 5% tolerance, SMD resistor, Vishay Intertechnology, Inc., Malvern, Pa., USA) may be coupled in parallel with resonator 28 (Y1) to stabilize the frequency of resonator 28 (Y1).

A bypass capacitor 20 (C3) (e.g., a model CL03A105MP3NSNC, 1-µF, 10-volt, 20% tolerance, X5R dielectric, and 0201 size tantalum capacitor, Samsung Electro-Mechanics America, Inc., Irvine, Calif., USA) may be coupled to controller 6 and power source 10 to filter electronic noise and current spikes stemming from components on circuit board 2. As will be appreciated by those of ordinary skill in the art, electrical components may be positioned where needed. No limitations are intended.

Figure 4B:
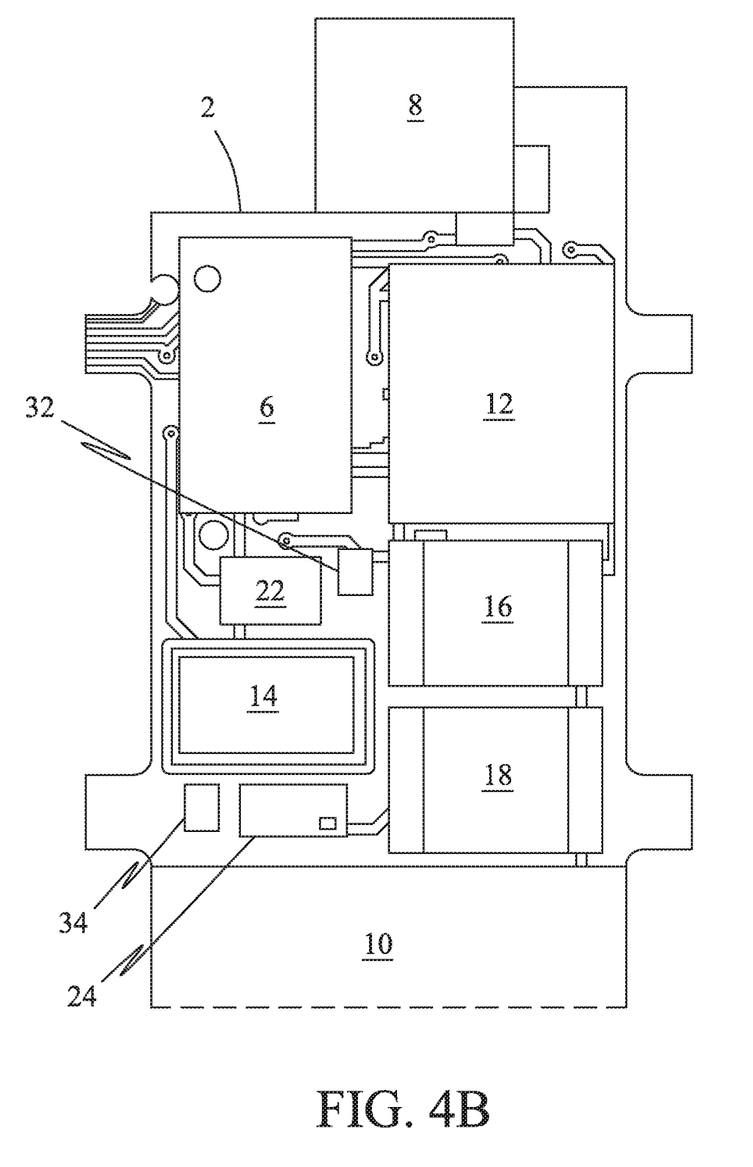

FIGS. 4A-4B are different bottom-side views of circuit board 2 showing position of selected components of acoustic tag 100. Piezoelectric transducer 8 and power source 10 may be coupled as described previously (see FIG. 3A-3B).

Microcontroller 6 (U1) may control operation of the components of the tag. In the exemplary embodiment, microcontroller 6 (U1) is shown positioned adjacent piezoelectric transducer 8, but position is not intended to be limited thereto.

A first transistor 22 (Q1) (e.g., a model PMZB350UPE-315, 20-volt, p-channel MOSFET, NXP Semiconductors, San Jose, Calif., USA), a first capacitor 16 (C1) (e.g., a 47 uF, 10-volt, 20% tolerance, X5R dielectric, and 0805 size ceramic capacitor, TDK Corp., Minato, Tokyo, JP), and an inductor 14 (L2) (e.g., a 10 uH, 80 MAmp, 20% tolerance, and 0603 size inductor, TDK Corp., Minato, Tokyo, JP) are components of the dual boost converter sub-circuit 36. These components generate the negative output voltage (e.g., about −3 volts), and couple electrically to analog switches 40 (U2) and 42 (U3) described previously in reference to FIG. 2 and FIGS. 3A-3B.

A second transistor 24 (Q2) (e.g., a 30-volt, 1.78 A, N-channel MOSFET, Fairchild Semiconductor, Inc., Dallas, Tex., USA) and a second capacitor 18 (C2) (e.g., a 47 uF, 10-volt, 20% tolerance, X5R dielectric, and 0805 size ceramic capacitor, TDK Corp., Minato, Tokyo, JP), are additional components of the dual boost converter sub-circuit 36. These components share inductor 14 (L2) described previously above and together generate the positive output voltage (e.g., about +7 volts), and couple electrically to analog switches 40 (U2) and 42 (U3) described previously in reference to FIG. 2 and FIGS. 3A-3B.

Analog switch 42 (U3) may couple to piezoelectric transducer 8 through inductor 12 (L1) to increase the drive voltage across the piezoelectric transducer.

In FIG. 4B, a first diode 32 (D1) (e.g., a 30-volt, 0.1 A, 2DFN Schottky Diode 0201, Diodes, Inc., Plano, Tex., USA) and a second diode 34 (D2) (e.g., a 30-volt, 0.1 A, 2DFN Schottky Diode 0201, Diodes, Inc., Plano, Tex., USA) are additional components of the dual boost converter sub-circuit 36. First diode 32 (D1) assists in the generation of the negative voltage (e.g., –3 volts), and second diode 34 (D2) assists in the generation of the positive voltage (e.g., +7 volts).

Tag Circuit

Figure 5:
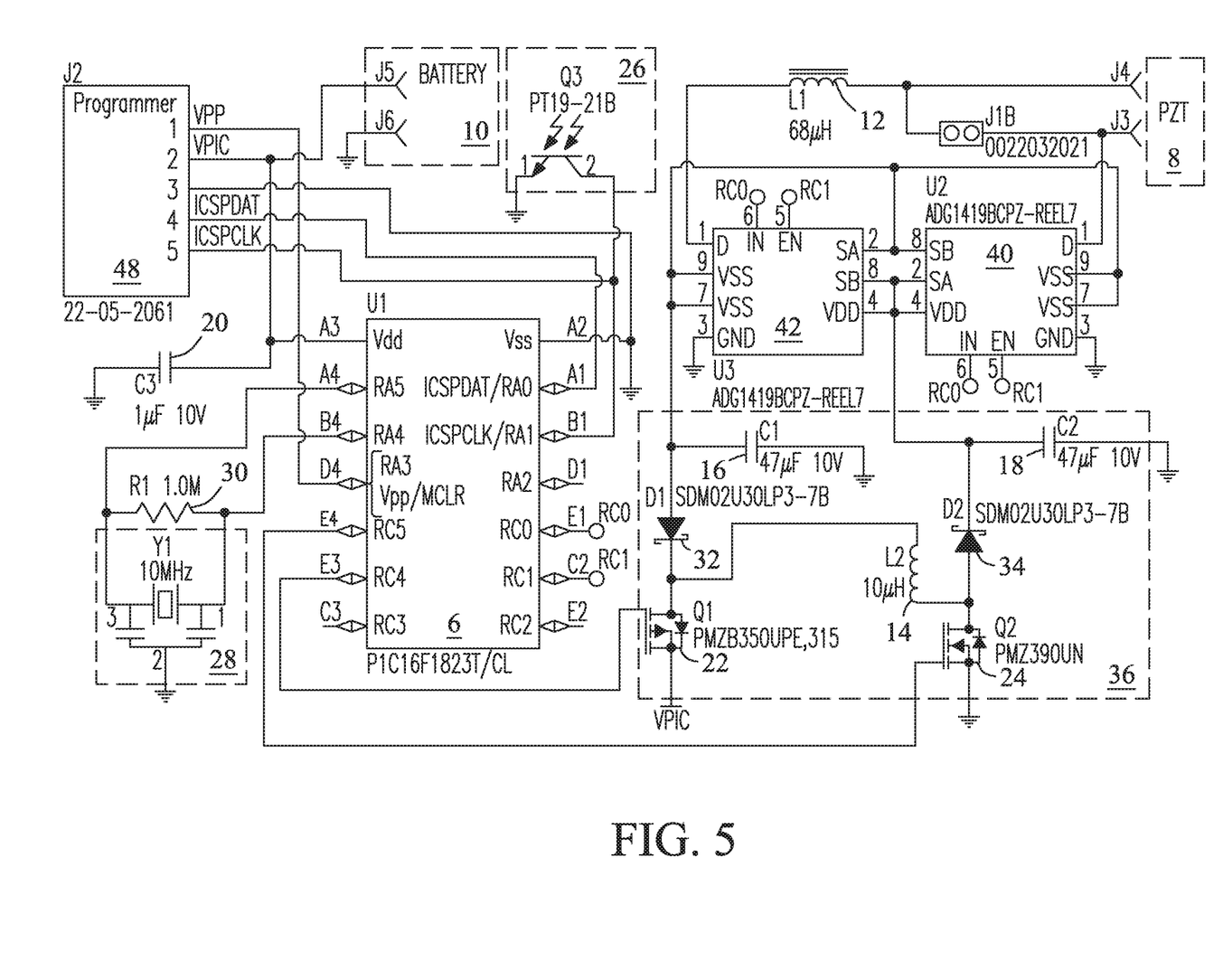
FIG. 5 shows a circuit diagram of the acoustic transmission device of the present invention.

FIG. 5 shows an exemplary tag circuit for acoustic tags of the present invention showing components described previously above. Components may be located on, or coupled to, a circuit board described previously in reference to FIG. 2. The tag circuit may include preferred trace line widths of about 0.01 cm (0.003 inches), but are not intended to be limited.

Configuration commands for programming microcontroller 6 may be received directly from an external computer (not shown), e.g., through an Integrated Circuit Serial Programmer (ICSP) module 48 (e.g. a MPLAB ICD 3 programmer, Microchip Technologies, Chandler, Ariz., USA) that couples to microcontroller 6. Programmer (ICSP) module 48 may couple to the external computer through a programming connector (e.g., a model 22-05-2061, 6-position connector, Molex Connector Corp., Lisle, Ill., USA) (not shown). The programming connector may be detached from the circuit board during assembly of the acoustic tag to reduce the final volume of the assembled tag.

Configuration and programming information may also be delivered remotely (e.g., optically) from the external computer through phototransistor 26 (Q3) and into controller 6 through a selected input pin. Pins are not intended to be limited.

Bypass capacitor 20 (C3) may be coupled to controller 6 and power source 10 to filter electronic noise and current spikes from components on the circuit board.

Resonator 28 (Y1) delivers a clock signal that controls the timing of delivery of a positive channel drive signal (PCH-DRV) and a negative channel drive signal (NCH-DRV) to dual boost converter sub-circuit 36 described hereafter. A resistor 30 (R1) may be placed in parallel with resonator 28 (Y1) to stabilize the frequency and clock signal of resonator 28 (Y1).

Dual boost converter sub-circuit 36 may include a first transistor 22 (Q1), an inductor 14 (L2), a first diode 32 (D1), and a first capacitor 16 (C1) that together generate a negative output voltage (e.g., –3 volts). Microcontroller 6 may toggle the PCH-DRV signal to alternately build up current through inductor 14 (L2), and then discharges capacitor 16 (C1) through diode 32 (D1). Magnitude of the positive output voltage depends in part on the length of time that microcontroller 6 toggles the PCH-DRV signal. Microcontroller 6 may hold the NCH-DRV signal at a positive voltage during operation so that a second transistor 24 (Q2) described hereafter can conduct current.

Dual boost converter sub-circuit 36 may include second transistor 24 (Q2), inductor 14 (L2), second diode 34 (D2), and second capacitor 18 (C2) that together generate a positive output voltage (e.g., +7 volts). Microcontroller 6 toggles the NCH-DRV signal to alternately build up current through inductor 14 (L2), and then charge capacitor 18 (C2) through diode 34 (D1). The magnitude of the positive output voltage generally depends on the length of time that the microcontroller toggles the NCH-DRV signal. Microcontroller 6 (U1) may hold the PCH-DRV signal at zero voltage during this operation so that first transistor 22 (Q1) can conduct current.

Dual boost converter sub-circuit 36 may couple to two analog switches 40 (U2) and 42 (U3). The two analog switches respectively receive the positive and negative output voltages from the dual boost converter sub-circuit 36. The analog switches switch between these two voltages alternately in succession, under the control of microcontroller 6 (U1), to generate a selected (drive) voltage from the tag circuit that is delivered to piezoelectric transducer 8. Analog switch 40 (U2) may couple to one terminal (e.g., negative terminal) of piezoelectric transducer 8. Analog switch 42 (U3) may couple through a resonance inductor 12 (L1) to another terminal (e.g., positive terminal) of piezoelectric transducer 8. The drive voltage may be delivered from analog switch 42 (U3) through resonance inductor 12 (L1) to piezoelectric transducer 8 to generate the acoustic signal transmitted from piezoelectric transducer 8. Resonance inductor 12 (L1) is configured to increase the voltage delivered at the terminals of piezoelectric transducer 8. The acoustic signal transmitted from piezoelectric transducer 8 may have a selected modulation frequency (e.g., 416.7 kHz). The value of inductor 12 (L1) may be selected such that the inductance partially or fully cancels out characteristic capacitances of piezoelectric transducer 8 at the selected modulation frequency. The resulting voltage at each terminal of piezoelectric transducer 8 may go above the positive drive voltage and below the negative drive voltage. As will be appreciated by those of ordinary skill in the art, modulation frequencies may be varied and hence are not intended to be limited to the exemplary value described herein.

Tag Lifetimes

Lifetimes of acoustic tags of the present invention depend in part on the size of the power source (battery) 10 described previously in reference to FIG. 5. However, for a given power source size, in general, tag lifetimes are selectable by selecting: 1) the PRI for transmission of the acoustic signal, 2) the intensity of the acoustic signal, or 3) both the PRI and the intensity of the acoustic signal.

Within the selectable range of acoustic intensity between about 159 dB and about 163 dB, tag lifetimes may be estimated from empirical equation [1]:

$$T = \frac{V_{batt} * C_{batt} * I_0 * 1000}{130 + 35 * 10^{\frac{SL-155}{10}} + V_{batt} * I_S * t_0} * \frac{1}{24} \quad [1]$$

Here, lifetime (T) has units of days. ($V_{batt}$) is the battery voltage and has units of volts. ($C_{batt}$) is the battery capacity in units of milli-Amp-Hours (mAh). (SL) is the acoustic intensity (or source level) in units of dB. ($I_s$) is the constant static current that flows through the tag circuit (FIG. 5) in units of micro-Amps. ($t_0$) is the PRI in units of seconds. TABLE 2 lists exemplary constants that may be employed for calculating tag lifetimes (T) at a PRI ($t_0$) of 5 seconds and a signal strength (intensity) of 163 dB:

TABLE 2

| Item | Values |
|---|---|
| $V_{batt}$ | 3.0 V |
| $C_{batt}$ | 56 mAh |
| SL | 163 dB |
| $t_0$ | 5 seconds |
| $I_s$ | 0.4 µA |

From Equation [1], tag lifetime (T) may be calculated at about 98 days using identified variable values. Acoustic tags of the present invention are configured to maintain a selected energy expenditure ($e_{pulse}$) for each transmission of the acoustic signal even as battery voltage decreases gradually over time. Energy expenditure ($e_{pulse}$) values may be less than or equal to about 385 µJ per transmission at a signal intensity of 163 dB, and less than or equal to about 283 µJ per transmission at a signal intensity of 161 dB.

Actual tag lifetimes (T) may be longer than calculated lifetimes based on nominal energy expenditure ($e_{pulse}$) values. As an example, at a signal intensity (strength) setting of 163 dB, an empirical energy consumption value of 351 µJ per transmission may be used instead of the nominal 385 µJ for a more accurate estimate of tag lifetime. In another example, at a signal strength setting of 161 dB, an empirical energy consumption value of 269 µJ may be used instead of the nominal 283 µJ.

TABLE 3 lists experimental and projected tag lifetimes for acoustic tags of the present invention at selected PRIs and selected signal intensities.

TABLE 3

| PRI ($t_0$) (seconds) | | 0.5 | 1 | 5 | 10 | 15 |
|---|---|---|---|---|---|---|
| Tag | @163 dB | 8.9 | 19.9 | 98 | 193 | 285 |
| Lifetime (T) | @161 dB | 12.9 | 25.9 | 127 | 249 | 365 |
| (days) | | | | | | |
| Note: | | Experimental values | ---------Projected values--------- | | | |

Lifetimes (T) of acoustic tags of the present invention are selectable. Shorter tag lifetimes and longer tag lifetimes may be selected. In the table, it can be seen that for a selected signal intensity, tag lifetime may be selected by varying the PRI. For example, at a signal intensity of 163 dB, tag lifetime corresponding to a 5 sec PRI is about 98 days; tag lifetime corresponding to a 15 sec PRI is about 285 days. It will be readily understood by those of ordinary skill in the art that various signal intensities may be selected with their corresponding lifetimes at selected PRIs to meet specific tracking needs for selected hosts and/or for selected applications. No limitations are intended. For example, for a tag with a signal intensity set at 161 dB, tag lifetime may be at least about 12.9 days using a PRI of 0.5 seconds, at least about 127 days using a PRI of 5 seconds, or about 365 days using a PRI of 15 seconds.

Beam Transmission Patterns

Beam transmission patterns of the piezoelectric transducer are described, e.g., in U.S. application Ser. No. 14/014,035 filed 29 Aug. 2013.

Transmission Detection Range

Acoustic signals transmitted by tags of the present invention may include selected detection ranges. Tag signals may be encoded to provide maximum strength and to improve range and resolution. In locations with a relatively small amount of background noise, such as the middle of a lake, signals may be transmitted up to about 500 meters. The present tag delivers a higher source level output to provide for the 500-meter detection range than used in previous tags. TABLE 4 lists projected detection ranges at two exemplary intensity values of 163 dB and 161 dB for three different signal transmission spread scenarios and an assumed noise level of 97 dB in a quiet environment (e.g. the forebay of a dam). However, no limitations are intended by the illustrative example.

TABLE 4

| | | Detection range (meters) | | |
|---|---|---|---|---|
| | | Spherical | Realistic* | Cylindrical |
| Forebay | @163 dB | 726 | 512 | 770 |
| | @161 dB | 249 | 475 | 277 |

*A noise level of 97 dB is presumed based on actual noise level measurements.

Data suggest a transmission detection range of 500 meters or better may be achieved at an acoustic signal intensity selected from 159 dB to 163 dB. In locations with larger background noise (e.g., immediately downstream of a dam spillway), signals may be transmitted about 100 meters. However, distances are not intended to be limited.

Coding and Activation

Tags of the present invention may be programmed with one or more tag codes of a selectable code length. The microcontroller (FIG. 2) may also contain internal sensors such as temperature sensors that collect additional data from the host and surrounding environment. As an example, a 5-bit temperature value or other sensor values with selected bit-lengths may be input from selected sensors into one or more tag codes that are then transmitted from the piezoelectric transducer. Coding and sensors are described in U.S. application Ser. No. 14/014,035 filed 29 Aug. 2013.

Methods and locations for attachment of acoustic tags to selected hosts are not limited. Acoustic tags may be attached, e.g., to the outside of the host (e.g., to the clothing or scuba gear of a human host), to an inanimate object, to a self-propelled object such as a robot, attached internally to the host (e.g., inserted within an object, surgically implanted, or injected). No limitations are intended.

Applications for acoustic tags of the present invention may include, but are not limited to, e.g., survival studies; monitoring migration/passage/trajectories; tracking host behavior or location in two dimensions (2D) or three dimensions (3D); measuring bypass effectiveness at dams and other passages; observing predator/prey dynamics; helping public utility agencies, private firms, and state and federal agencies meet fishery or other regulations; and other applications. Applications are not intended to be limited.

The present invention delivers unsurpassed advantages not obtained in previous designs and open up a broad array of tag uses and applications not yet realized. The high-efficiency piezoelectric transducer drive circuit in the instant design enhances energy conversion efficiency and reduces number of dedicated components, all while maintaining the same source level performance. Fewer components decreases the energy required to power the tag, which permits yet smaller acoustic tags with a lower mass to be constructed for even smaller hosts and applications.

While the invention has been described with what is presently considered to be the most practical and preferred embodiments, many changes, modifications, and equivalent arrangements may be made without departing from the invention in its true scope and broader aspects. Thus, the scope is expected to be accorded the broadest interpretation relative to the appended claims. The appended claims are therefore intended to cover all such changes, modifications, equivalent structures, and products as fall within the scope of the invention. No limitations are intended.

What is claimed is:

1. An acoustic transmission (tag) device, comprising:
a power source;
a tag circuit;
a piezoelectric transducer;
a housing configured to be associated with a host to be tracked and wherein the housing is coupled with the power source, the tag circuit and the piezoelectric transducer;
wherein the power source delivers a power source voltage to power the tag circuit;
wherein the tag circuit comprises:
a dual boost converter sub-circuit coupled with the power source and configured to receive the power source voltage; and
a plurality of switches individually coupled with the dual boost converter sub-circuit and the piezoelectric transducer, wherein each of the switches is configured to selectively apply electrical energy received from the dual boost converter sub-circuit to the piezoelectric transducer; and
wherein the switches are coupled with different terminals of the piezoelectric transducer.

2. The acoustic device of claim 1, further comprising an inductor coupled with one of the switches and one of the terminals of the piezoelectric transducer.

3. The acoustic device of claim 1, wherein the dual boost converter sub-circuit generates voltage potentials that alternate between about −3 volts and about +7 volts.

4. The acoustic device of claim 1, wherein the tag circuit delivers a selected voltage to the piezoelectric transducer that is at least about 20 volts (peak-to-peak).

5. The acoustic device of claim 1, wherein the dual boost converter sub-circuit comprises a plurality of output terminals coupled with the switches, and wherein the dual boost converter sub-circuit is configured to output different voltages via the output terminals.

6. The acoustic device of claim 5, wherein the different voltages have different electrical polarities.

7. The acoustic device of claim 5, wherein one of the voltages outputted via one of the output terminals is greater than the power source voltage and another of the voltages outputted via another of the output terminals is less than the power source voltage.

8. The acoustic device of claim 1, wherein the tag has a volume of about 429 mm$^3$ or less.

9. The acoustic device of claim 1, wherein the tag has a mass of about 720 mg or less in air.

10. The acoustic device of claim 1, wherein the housing is configured to be received within the host to be tracked.

11. A method for tracking a selected host, comprising:
associating an acoustic transmission (tag) device with a selected host to be tracked;
while the acoustic transmission (tag) device is associated with the host, delivering electrical energy from a tag circuit to a piezoelectric transducer in the acoustic transmission (tag) device to generate an acoustic transmission signal;
wherein the delivering comprises delivering using a plurality of switches individually configured to selectively deliver the electrical energy from a dual boost converter sub-circuit to the piezoelectric transducer;
while the acoustic transmission (tag) device is associated with the host, transmitting the acoustic transmission signal from the piezoelectric transducer externally of the host; and
wherein the delivering comprises delivering at least some of the electrical energy using an inductor coupled with one of the switches and the piezoelectric transducer.

12. The method of claim 11, wherein the switches are coupled with different terminals of the piezoelectric transducer.

13. The method of claim 11, wherein the delivering the electrical energy includes generating voltage potentials in the dual boost converter sub-circuit that alternate between about −3 volts and about +7 volts.

14. The method of claim 11, wherein the delivering the electrical energy includes delivering a voltage of at least about 20 volts (peak-to-peak).

15. The method of claim 11, wherein the delivering the electrical energy comprises outputting a plurality of voltages via a plurality of output terminals of the dual boost converter sub-circuit.

16. The method of claim 15, wherein the voltages have different electrical polarities.

17. The method of claim 15, further comprising supplying a power source voltage from a power source to the tag circuit, and wherein one of the voltages outputted via one of the output terminals is greater than the power source voltage and another of the voltages outputted via another of the output terminals is lower than the power source voltage.

18. The method of claim 11, wherein the tag has a volume of about 429 mm$^3$ or less.

19. The method of claim 11, wherein the tag has a mass of about 720 mg or less in air.

20. The method of claim 11, wherein the associating comprises providing the tag within the host to be tracked.

21. An acoustic transmission (tag) device, comprising:
a power source;
a tag circuit;
a piezoelectric transducer;
a housing configured to be associated with a host to be tracked and wherein the housing is coupled with the power source, the tag circuit and the piezoelectric transducer;
wherein the power source delivers a power source voltage to power the tag circuit; and
wherein the tag circuit comprises:
- a dual boost converter sub-circuit coupled with the power source and configured to receive the power source voltage;
- a plurality of switches individually coupled with the dual boost converter sub-circuit and the piezoelectric transducer, wherein each of the switches is configured to selectively apply electrical energy received from the dual boost converter sub-circuit to the piezoelectric transducer; and
- an inductor coupled with one of the switches and a terminal of the piezoelectric transducer.

22. A method for tracking a selected host, comprising:
associating an acoustic transmission (tag) device with a selected host to be tracked;
while the acoustic transmission (tag) device is associated with the host, delivering electrical energy from a tag circuit to a piezoelectric transducer in the acoustic transmission (tag) device to generate an acoustic transmission signal;
wherein the delivering comprises delivering using a plurality of switches individually configured to selectively deliver the electrical energy from a dual boost converter sub-circuit to the piezoelectric transducer;
while the acoustic transmission (tag) device is associated with the host, transmitting the acoustic transmission signal from the piezoelectric transducer externally of the host; and
wherein the switches are coupled with different terminals of the piezoelectric transducer.

* * * * *

UNITED STATES PATENT AND TRADEMARK OFFICE
CERTIFICATE OF CORRECTION

Page 1 of 4

PATENT NO. : 10,739,434 B2
APPLICATION NO. : 16/143273
DATED : August 11, 2020
INVENTOR(S) : Zhiqun Deng et al.

It is certified that error appears in the above-identified patent and that said Letters Patent is hereby corrected as shown below:

On the Title Page

Item (56) References Cited, Page 2, 2nd column, 50th Line – Replace:
"PCT/US2014/05357 B 12/2014" with --PCT/US2014/053578 12/2014--

Item (56) References Cited, Page 3, 1st Column, 37th Line – Replace:
"Hwang et al., "Powered Cardiac Pacemaker Enabled by Flexible" with --Hwang et al., "Self-Powered Cardiac Pacemaker Enabled by Flexible--

Item (56) References Cited, Page 3, 2nd Column, 32nd Line – Replace:
"Angela et al., "Effects of Acoustic Transmitters on Swimming" with --Anglea et al., "Effects of Acoustic Transmitters on Swimming--

Item (56) References Cited, Page 2 – Add:
8,922,373        12/2014      Michelson
10,236,920       3/2019       Deng et al.
2003/0034887     2/2003       Crabtree et al.
2011/0077659     3/2011       Mandecki et al.
2015/0351365     12/2015      Claver Tallon et al.
2019/0056372     2/2019       Deng et al.
2019/0103888     4/2019       Deng et al.

Item (56) References Cited, Page 2 – Add:
CN    101714207          5/2010
CN    2015800768080      11/2019
WO    PCT/US2017/038082  2/2019

Item (56) References Cited, Page 3 – Add:
Brown, "The Effects of Material Selection for Backing and Wear Protection/Quarter-Wave Matching of Piezoelectric Polymer Ultrasound Transducers", IEEE Ultrasonics Symposium, 2000, Signed and Sealed this
Second Day of September, 2025

Coke Morgan Stewart
*Acting Director of the United States Patent and Trademark Office*

United States, pages 1029-1032.
Butler et al., "A Tri-Modal Directional Modem Transducer", Oceans 2003 MTS/IEEE Conference, September 22-26, 2003, United States, pages 1554-1560.
Cada, "The Development of Advanced Hydroelectric Turbines to Improve Fish Passage Survival", Fisheries Vol. 26, No. 9, September 2001, United States, pages 14-23.
Carlson et al., "Juvenile Salmon Acoustic Telemetry System Transmitter Downsize Assessment", Pacific Northwest National Laboratory, Richland, WA, 2010, United States, 30 pages.
Carlson et al., "Sensor Fish Characterization of Spillway Conditions at Ice Harbor Dam in 2004, 2005 and 2006", PNWD-3839 Final Report, March 2008, United States, 95 pages.
Carlson et al., "The Sensor Fish - Making Dams More Salmon-Friendly", Sensors Online, July 2004, United States, 7 pages.
Collins et al., "Intracoelomic Acoustic Tagging of Juvenile Sockeye Salmon: Swimming Performance, Survival, and Postsurgical Wound Healing in Freshwater and during a Transition to Seawater", Transactions of the American Fisheries Society 142, 2013, United States, pages 515-523.
Cote et al., "Swimming Performance and Growth Rates of Juvenile Atlantic Cod Intraperitoneally Implanted with Dummy Acoustic Transmitters", North American Journal of Fisheries Management Vol. 19, 1999, United States, pages 1137-1141.
Counihan et al., "Influence of Externally Attached Transmitters on the Swimming Performance of Juvenile White Sturgeon", Transactions of the American Fisheries Society 128, 1999, United States, pages 965-970.
Coutant, "Fish Behavior in Relation to Passage Through Hydropower Turbines: A Review", Transactions of the American Fisheries Society Vol. 129, 2000, United States, pages 351-380.
Deng et al., "Design and Implementation of a New Autonomous Sensor Fish to Support Advanced Hydropower Development", Review of Scientific Instruments Vol. 85, 2014, United States, 6 pages.
Deng et al., "Evaluation of Fish-Injury Mechanisms During Exposure to Turbulent Shear Flow", Canadian Journal of Fisheries and Aquatic Sciences Vol. 62, 2005, Canada, pages 1513-1522.
Deng et al., "Six-Degree-of-Freedom Sensor Fish Design and Instrumentation", Sensors Vol. 7, 2007, United States, pages 3399-3415.
Deng et al., "Use of an Autonomous Sensor to Evaluate the Biological Performance of the Advanced Turbine at Wanapum Dam", Journal of Renewable and Sustainable Energy Vol. 2, 2010, United States, 11 pages.
Deng et al., U.S. Patent Application Serial No. 16/056,185, filed August 6, 2018, titled "Autonomous Sensor Fish to Support Advanced Hydropower Development", 36 pages.
Dillon, "Use and Calibration of the Internal Temperature Indicator", Microchip Technology Inc. AN1333, 2010, United States, 12 pages.
Dinwoodie, "Dual Output Boost Converter", Texas Instruments Application Report SLUA288, available online at http://www.ti.com/lit/an/slua288/slua288.pdf, April 2003, 9 pages.
El Rifai et al., "Modeling of Piezoelectric Tube Actuators", Dspace@MIT: Innovation in Manufacturing Systems and Technology (IMST), 2004, Singapore, 9 pages.
Fisheries and Oceans Canada (DFO), "Recovery Potential Assessment of American Eel (Anguilla rostrata) in Eastern Canada", Canadian Science Advisory Secretariat Science Advisory Report 2013/078, 2013, Canada, 65 pages.
Gallego-Juarez et al., "Experimental Study of Nonlinearity in Free Progressive Acoustic Waves in Air at 20 kHz", Journal de Physique, Colloques, 40 (C8), 1979, France, pages 336-340.
Harnish et al., "A Review of Polymer-Based Water Conditioners for Reduction of Handling-Related Injury", Reviews in Fish Biology and Fisheries 21, 2011, Netherlands, pages 43-49.

Janak et al., "The Effects of Neutrally Buoyant, Externally Attached Transmitters on Swimming Performance and Predator Avoidance of Juvenile Chinook Salmon", Transactions of the American Fisheries Society 141, 2012, United States, pages 1424-1432.
Johnson et al., "A Digital Acoustic Recording Tag for Measuring the Response of Wild Marine Mammals to Sound", IEEE Journal of Oceanic Engineering Vol. 28, No. 1, January 2003, United States, pages 3-12.
Kogan et al., "Acoustic Concentration of Particles in Piezoelectric Tubes: Theoretical Modeling of the Effect of Cavity Shape and Symmetry Breaking", The Journal of the Acoustical Society of America Vol. 116, No. 4, 2004, United States, pages 1967-1974.
Lewandowski et al., "In Vivo Demonstration of a Self-Sustaining, Implantable, Stimulated-Muscle-Powered Piezoelectric Generator Prototype", Annals of Biomedical Engineering Vol. 37, No. 11, November 2009, Netherlands, pages 2390-2401.
Li et al., "Piezoelectric Materials used in Underwater Acoustic Transmitters", Sensor Letters Vol. 10, 2012, United States, 65 pages.
MacGregor et al., "Recovery Strategy for the American Eel (Anguilla rostrata) in Ontario", Ontario Recovery Strategy Series, Prepared for Ontario Ministry of Natural Resources, Peterborough, Ontario, 2013, Canada, 131 pages.
McGrath et al., "Studies of Upstream Migrant American Eels at the Moses-Saunders Power Dam on the St. Lawrence River near Massena, New York", American Fisheries Society Symposium 33, 2003, United States, pages 153-166.
Mesa et al., "Survival and Growth of Juvenile Pacific Lampreys Tagged with Passive Integrated Transponders (PIT) in Freshwater and Seawater", Transactions of the American Fisheries Society 141, 2012, United States, pages 1260-1268.
Mueller et al., "Tagging Juvenile Pacific Lamprey with Passive Integrated Transponders: Methodology, Short-Term Mortality, and Influence on Swimming Performance", North American Journal of Fisheries Management Vol. 26, 2006, United States, pages 361–366.
Normandeau, "Survey for Upstream American Eel Passage at Holyoke Dam, Connecticut River, Massachusetts, 2006", Prepared for Holyoke Gas and Electric by Normandeau Associates, Inc., April 26, 2007, United States, 68 pages.
Odeh, "A Summary of Environmentally Friendly Turbine Design Concepts", DOE/ID/13741 Paper, July 1999, United States, 47 pages.
Økland et al., "Recommendations on Size and Position of Surgically and Gastrically Implanted Electronic Tags in European Silver Eel", Animal Biotelemetry 1:6, 2013, United Kingdom, pages 1-5.
Pacific Northwest National Laboratory, "JSATS Tag Downsize Project Progress Report", PNNL, April 26, 2010, United States, 16 pages.
Pacific Northwest National Laboratory, "Juvenile Salmon Acoustic Telemetry System (JSATS) Acoustic Transmitters", PNNL, March 2010, United States, 1 page.
Panther et al., "Influence of Incision Location on Transmitter Loss, Healing, Survival, Growth, and Suture Retention of Juvenile Chinook Salmon", Transactions of the American Fisheries Society 140, 2011, United States, pages 1492-1503.
Platt et al., "The Use of Piezoelectric Ceramics for Electric Power Generation Within Orthopedic Implants", IEEE/ASME Transactions on Mechatronics Vol. 10, No. 4, August 2005, United States, pages 455-461.
Richmond et al., "Response Relationships Between Juvenile Salmon and an Autonomous Sensor in Turbulent Flow", Fisheries Research Vol. 97, 2009, Netherlands, pages 134-139.
Rifai et al., "Modeling of Piezoelectric Tube Actuators", Dspace@MIT, available online at https://dspace.mit.edu/bitstream/handle/1721.1/3911/IMST014.pdf, 2004, 8 pages.
Summerfelt et al., "Anesthesia, Surgery, and Related Techniques", in Schreck, C.B., Moyle, P.B., (Eds.), Methods for Fish Biology, American Fisheries Society, 1990, United States, pages 213-272.
Verdon et al., "Recruitment of American Eels in the Richelieu River and Lake Champlain: Provision of Upstream Passage as a Regional-Scale Solution to a Large-Scale Problem", American Fisheries Society Symposium 33, 2003, United States, pages 125-138.
Walker et al., "Effects of a Novel Acoustic Transmitter on Swimming Performance and Predator Avoidance of Juvenile Chinook Salmon: Determination of a Size Threshold", Fisheries Research 176, 2016, Netherlands, pages 48-54.
Ward et al., "A Laboratory Evaluation of Tagging-Related Mortality and Tag Loss in Juvenile Humpback Chub", North American Journal of Fisheries Management 35, 2015, United States, pages 135-140.
Wuenschel et al., "Swimming Ability of Eels (Anguilla rostrata, Conger oceanicus) at Estuarine Ingress: Contrasting Patterns of Cross-Shelf Transport?", Marine Biology 154, 2008, Germany, pages 775-786.
Zale et al., "Effects of Surgically Implanted Transmitter Weights on Growth and Swimming Stamina of Small Adult Westslope Cutthroat Trout", Transactions of the American Fisheries Society Vol. 134(3), 2005, United States, pages 653-660.
Deng et al., U.S. Patent Application Serial No. 16/351,373, filed March 12, 2019, titled "Sensor Assemblies and Methods for Emulating Interaction of Entities Within Water Systems", 30 pages.
Brown, "Power Sources and Supplies", ISBN 978-7-5124-1052-7, October 2013, China, 5 pages plus English translation.
China Electrical Appliance Industrial Institute, Editor of "Electrical and Electronic Technologies", Collection of Translations of Articles in 1992 International Electrical and Electronic Academic Conference, November 1993, China, page 540 plus English translation.
Deng et al., U.S. Patent Application Serial No. 16/726,574, filed December 24, 2019, titled "Systems and Methods for Monitoring Organisms Within an Aquatic Environment", 49 pages.